United States Patent

Tanaka et al.

Patent Number: 5,174,989
Date of Patent: Dec. 29, 1992

[54] ORAL COMPOSITION

[75] Inventors: Kumiko Tanaka; Seishiro Fujii, both of Yokohama, Japan

[73] Assignee: Shiseido Company Ltd., Tokyo, Japan

[21] Appl. No.: 572,326

[22] Filed: Aug. 21, 1990

Related U.S. Application Data

[63] Continuation of Ser. No. 250,466, Sep. 28, 1988, abandoned.

Foreign Application Priority Data

Nov. 25, 1987 [JP] Japan ............... 62-296374

[51] Int. Cl.$^5$ .............. A61K 7/16; A61K 7/18; A61K 7/22
[52] U.S. Cl. ..................... 424/52; 424/49; 424/51; 424/54; 131/270
[58] Field of Search ............ 424/49, 52, 51, 54; 131/270

[56] References Cited

U.S. PATENT DOCUMENTS

| | | | |
|---|---|---|---|
| Re. 30,309 | 6/1980 | Cousse et al. | 424/52 |
| 3,877,468 | 4/1975 | Lichtneckert et al. | 131/270 |
| 3,992,519 | 11/1976 | Hofmann et al. | 424/52 |
| 4,064,138 | 12/1977 | Saari et al. | 424/52 |
| 4,098,879 | 7/1978 | Cousse et al. | 424/52 |
| 4,161,518 | 7/1979 | Wen et al. | 424/52 |
| 4,170,636 | 10/1979 | Engel et al. | 424/52 |
| 4,276,890 | 7/1981 | Fichera | 131/270 |
| 4,311,691 | 1/1982 | Fichera | 131/270 |
| 4,391,798 | 7/1983 | Tavss et al. | 424/52 |
| 4,474,749 | 10/1984 | Kruppa | 424/52 |
| 4,515,771 | 5/1985 | Fine | 424/52 |
| 4,579,858 | 4/1986 | Fernö et al. | 131/270 |
| 4,672,032 | 6/1987 | Slavkin et al. | 424/52 |
| 4,749,561 | 6/1988 | Lane et al. | 424/49 |
| 4,749,562 | 6/1988 | Lane et al. | 424/49 |
| 4,867,181 | 9/1989 | Smolko | 131/270 |
| 4,907,605 | 3/1990 | Ray et al. | 131/270 |

FOREIGN PATENT DOCUMENTS 0049830 4/1982 European Pat. Off. .

*Primary Examiner*—Ronald W. Griffin
*Attorney, Agent, or Firm*—Sprung Horn Kramer & Woods

[57] ABSTRACT

An oral composition comprising (i) at least one fluoride compound and (ii) at least one 5- or 6-membered, substituted heterocyclic compound which contains 1 to 3 nitrogen atoms as ring hetero atoms, which may contain an oxygen or sulfur atom as a ring hetero atom, and which may be condensed with one or two 6-membered carbocyclic or heterocyclic rings, or a salt thereof. This oral composition is very effective for preventing carries of the teeth.

10 Claims, No Drawings

ORAL COMPOSITION

This is a continuation of application Ser. No. 07/250,466 filed Sep. 28, 1988 now abandoned.

BACKGROUND OF THE INVENTION

1. Field of the Invention

The present invention relates to an oral composition. More particularly, the present invention relates to an oral composition which can considerably enhance a preventive effect for caries of the teeth, in comparison with a conventional oral composition.

2. Description of the Related Art

An effect of the fluoride compound is widely known in preventing caries of the teeth. Caries is a phenomenon whereby a tooth is decalcified by an action of organic acids such as lactic acid formed from decomposition of sugars such as sucrose, by a microorganism present in an oral cavity, mainly *Streytococcus mutans*.

A hydroxyapatite is a main component of an enamel, and an uptake of a fluoride ion into a crystal lattice of hydroxyapatite is easily performed and the fluoride ion enhances crystallinity thereof. As a result, the tooth is reinforced, the enamel becomes more resistant to decalcification by the organic acid formed by the microorganism present in the oral cavity, and thus caries may be prevented. It is also believed that the uptake of the fluoride ion is more easily effected into a lesion of incipient caries (wherein some decalcification proceeds) than into a sound enamel, and thus enhances recalcification and inhibits the progress of caries.

To prevent caries, a fluoride compound such as sodium fluoride, sodium monofluorophosphate, or stannous fluoride has hitherto been added to tap water, or to a dentifrice, and topically applied to the tooth surface. Further, a mouth wash has been formulated with the fluoride compound.

Nevertheless, since caries is still wide-spread, conventional methods wherein only the fluoride compound is employed do not satisfactorily prevent caries, and there is a demand for a more effective method of caries prevention.

SUMMARY OF THE INVENTION

After conducting intensive research into a more effective prevention of caries, the present inventors found that, when the conventional fluoride compound is used in combination with one or more particular substituted nitrogen-heterocyclic compounds, the uptake of the fluoride ion into hydroxyapatite can be more easily effected, and thus the reinforcement action of the fluoride ion to the tooth is enhanced. The present invention is based on the above discovery.

Accordingly, an object of the present invention is to provide a novel oral composition which effectively prevents caries.

In accordance with the present invention, there is provided an oral composition comprising (i) at least one fluoride compound and (ii) at least one 5- or 6membered, substituted heterocyclic compound which contains 1 to 3 nitrogen atoms as ring hetero atoms, which may contain an oxygen or sulfur atom as a ring hetero atom, and which may be condensed with one or two 6-membered carbocyclic or heterocyclic rings, or a salt thereof.

DESCRIPTION OF THE PREFERRED EMBODIMENTS

The fluoride compound which may be used in the present invention is a compound containing a fluorine which is prevailingly present in the biological field. The fluoride compounds include an inorganic fluoride, such as an alkali metal fluoride such as sodium fluoride, potassium fluoride, lithium fluoride, or cesium fluoride; zirconium fluoride, ammonium fluoride, stannous fluoride; alkali metal monofluorophosphate such as sodium monofluorophosphate, or potassium monofluorophosphate; or alkali metal titanium fluoride such as sodium titanium fluoride or potassium titanium fluoride; and an organic fluoride compound such as a monoalkylamine hydrofluoride such as hexylamine hydrofluoride, laurylamine hydrofluoride, or cetylamine hydrofluoride; amino acid hydrofluoride such as glycine hydrofluoride, lysine hydrofluoride, or alanine hydrofluoride; or fluorosilane. The above fluoride compounds may be used singly or in combination thereof. From the viewpoint of oral application, sodium fluoride, potassium fluoride, ammonium fluoride, stannous fluoride, sodium monofluorophosphate or potassium monofluorophosphate is preferable.

The fluoride compound is incorporated in the oral composition according to the present invention in an amount of from about 50–10,000 ppm ($\mu$g/g), preferably about 200–10,000 ppm as a total fluorine concentration in the composition. If the amount is less than 50 ppm, a desired reinforcement action cannot be obtained. Although the fluoride compound may be used in the amount of more than 10,000 ppm, the desired effect does not increase as the amount increases, and thus it is not economical. When producing the dentifrice, the total fluorine concentration of 1,000 ppm or less is preferable.

The oral composition according to the present invention contains one or more 5- or 6-membered, substituted heterocyclic compound which contains 1 to 3 nitrogen atoms as ring hetero atoms, which may contain an oxygen or sulfur atom as a ring hetero atom, and which may be condensed with one or two 6-membered carbocyclic or heterocyclic rings, or a salt thereof.

Preferably, the above nitrogen-heterocyclic compound used in the present invention contains at least one —N=moiety in the molecule, and more preferably has an aromatic character.

The heterocyclic compound carries thereon one or more substituents. The substituents include, for example, a lower alkyl (e.g., methyl, ethyl, propyl, butyl), a lower alkoxy (e.g., methoxy, ethoxy, propoxy, butoxy), hydroxy, acyl (e.g., formyl, acetyl), lower alkoxy carbonyl (e.g., methoxy carbonyl, ethoxy carbonyl), carboxyl, carbamoyl, and amino groups. The above alkyl substituent may be further substituted with hydroxy, esterified hydroxy (e.g., hydroxy esterified by phosphoric acid), amino, carboxyl and/or cyclic imino (which may be interrupted by sulfur). Typical examples of the substituted alkyl groups are hydroxymethyl, methyl group having hydroxy group esterified with phosphoric acid, 2-amino-2-carboxyl-ethyl, and 2-(5-hydroxyethyl-4-methyl-1,3-thiazoline)-methyl.

The term "lower" used herein with respect to an alkyl, alkoxy group or the like means that such an alkyl or alkoxy group has 1–4 carbon atoms.

In the present invention, a 5- or 6-membered, substituted monocyclic compound which contains 1 to 3 nitrogen atoms as ring hetero atoms and may contain an oxygen or sulfur atom as a ring hetero atom may be used. The monocyclic compounds include imidazole, triazole, oxazole, triazole, pyridine, pyrimidine and oxazine. Those monocyclic compounds carry one or more substituents as mentioned above.

The preferred monocyclic compound is a pyridine derivative of the formula

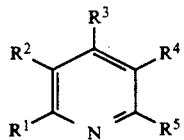
(1)

wherein $R^1$ represents a hydrogen or lower alkyl, $R^2$ represents a hydrogen or hydroxy, $R^3$ represents a hydrogen, lower alkyl, substituted lower alkyl (e.g., hydroxyalkyl, aminoalkyl) or acyl (e.g., formyl or other acyl groups derived from lower alkanoic acids), $R^4$ represents a hydrogen, lower alkyl, substituted lower alkyl (e.g., hydroxy alkyl, hydroxy alkyl esterified with phosphoric acid), carboxyl, carbamoyl or lower alkoxy carbonyl and $R^5$ represents a hydrogen, lower alkyl or substituted lower alkyl (e.g., hydroxyalkyl), with the proviso that at least one of $R^1$ to $R^5$ does not represent a hydrogen.

The typical monocyclic compounds include, for example, pyridoxine ($R^1$=CH$_3$, $R^2$=OH, $R^3$=CH$_2$OH, $R^4$=CH$_2$OH, and $R^5$=H) pyridoxal ($R^1$=CH$_3$, $R^2$=OH, $R^3$=CHO, $R^4$=CH$_2$OH, and $R^5$=H), and pyridoxamine ($R^1$=CH$_3$, $R^2$=OH, $R^3$=CH$_2$NH$_2$, $R^4$=CH$_2$OH, and $R^5$=H), a phosphoric ester thereof (e.g., $R^4$ in each compounds is esterified hydroxy methyl), a salt thereof (e.g., hydrochloride); 3-pyridylcarbinol ($R^1$=$R^2$=$R^3$=$R^5$=H, $R^4$=CH$_2$OH) or 2-pyridylcarbinol ($R^1$=$R^2$=$R^3$=$R^4$=H, and $R^5$=CH$_2$OH); nicotinic acid ($R^1$=$R^2$=$R^3$=$R^5$=H, and $R^4$=COOH), nicotinic ester ($R^1$=$R^2$=$R^3$=$R^5$=H, and $R^4$ is lower alkoxy carbonyl), nicotinic acid amide ($R^1$=$R^2$=$R^3$=$R^5$=H, and $R^4$=CONH$_2$).

Of those monocyclic compounds, pyridoxine hydrochloride, 3-pyridylcarbinol and 2-pyridylcarbinol are preferable.

Another preferred monocyclic compound is an imidazole or pyrimidine derivative of the formula

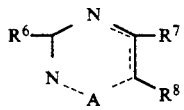
(2)

wherein A denotes a direct bond to form the imidazole nucleus or ring members —CH=necessary to form the pyrimidine nucleus, $R^6$ represents a hydrogen or lower alkyl, $R^7$ represents a hydrogen or amino, and $R^8$ represents lower alkyl or substituted lower alkyl (e.g., alkyl group substituted by carboxyl, amino and/or cyclic imino). The typical compounds of the formula (2) are histidine or a derivative thereof, preferably histidine hydrochloride, and thiamine or a derivative thereof, preferably thiamine hydrochloride.

In the present invention, a substituted bicyclic compound composed of a 5- or 6-membered heterocyclic compound having 2 nitrogen atoms as ring hetero atoms, and a condensed 6-membered carbocyclic or nitrogenheterocyclic compound may be employed. The bicyclic compound includes benzimidazole, purine, xanthine and quinazoline. Those bicyclic compounds carry one or more substituents as mentioned above.

In the present invention, a substituted tricyclic compound composed of a 6-membered heterocyclic compound having 1 or 2 nitrogen atoms as ring hetero atoms, and two condensed 6-membered carbocyclic compounds may be employed. Examples of the tricyclic compounds are phenazine, and preferably, acridine. These compounds carry one or more substituents as mentioned above. The preferred tricyclic compound is an acridine derivative, for example, acridine substituted with one or more amino or lower alkoxy, such as acrinol or a lactate thereof.

The above heterocyclic compounds may be used singly or in a combination thereof.

In the oral composition of the present invention, a molar ratio of the nitrogen-heterocyclic compound to the fluoride compound is about 1/50 to about 10/1, preferably about 1/10 to about 5/1, more preferably about 1/10 to about 3/1. If the molar ratio is less than 1/50, the desired reinforcement action of the fluoride cannot be obtained, whereas if the ratio is more than 10/1, the effect does not increase as the amount increases, and thus this is not economical.

In addition to the above two essential components, the present oral composition may contain various additives. The kinds of the additives depend on the types of oral composition. Examples of the additives are a polishing agent such as calcium phosphate (dibasic) dihydrate or anhydrate thereof, calcium phosphate (monobasic), calcium phosphate (tribasic), calcium carbonate, calcium pyrophosphate, titanium oxide, aluminum hydroxide, aluminum oxide, silica polishing agent (e.g., amorphous silica, crystalline silica, complex of alkali metal silicic anhydride), aluminum silicate, insoluble sodium metaphosphate, insoluble potassium metaphosphate, insoluble calcium polyphosphate, magnesium phosphate (tribasic), magnesium carbonate, magnesium sulfate, calcium sulfate, methyl polymethacrylate, bentonite, zirconium silicate, hydroxyapatite or synthetic polymer; a wetting agent such as glycerol, sorbitol, propylene glycol, polyethylene glycol, ethylene glycol, 1,3-butylene glycol, xylitol, maltitol, or lactitol; a thickening agent such as carboxymethyl cellulose, methyl cellulose, hydroxyethyl cellulose, sodium carboxymethylhydroxyethyl cellulose, sodium alginate, carrageenan, sodium polyacrylate, gum arabic, xanthan gum, tragacanth gum, karaya gum, polyvinyl alcohol, carboxyvinyl polymer, or polyvinyl pyrrolidone; an anionic surface active agent such as water soluble salt of C$_{8-18}$ alkyl sulfate (e.g., sodium lauryl sulfate, sodium myristyl sulfate), soluble higher fatty acid monoglyceride sulfate wherein the fatty acid has 10–18 carbon atoms (e.g., sodium lauryl monoglyceride sulfate, sodium coconut oil fatty acid monoglyceride sulfate, sodium higher fatty acid monoglyceride sulfate), α-olefin sulfate, paraffin sulfate, sodium salt of N-methyl-N-palmitoyl tauride, sodium N-lauryl sarcosinate sodium salt of N-lauroyl-β-alanine; a nonionic surface active agent such as fatty acid alkanol amide (e.g., lauric acid diethylamide), sucrose fatty acid ester (e.g., sucrose mono- or dilaurate), polyoxyethylene sorbitan fatty acid ester, polyoxyethylene fatty acid ester, polyoxyethylene hardened castor oil derivative, lactose fatty acid ester, maltitol fatty acid ester, or polyoxyethylene polyoxypropylene block copolymer; a cationic or amphoteric surface active agent; an oil such as higher alcohol or wax; a lower alcohol; an edulcorant such as sodium saccharin, stevioside, neohesperidin, dihydrochalcone, glycyrrhizin, perillartine, p-methoxycinnamic aldehyde; an essential oil such as peppermint, spearmint, or fennel; a perfume such as 1-menthol, carvone, eugenol, anethol or other perfume base; a colorant; a preservative; an antimold agent; an antioxidant; and water. Further, the present oral composition may contain ingredients usually incorporated in an oral composition, for example, dextranase, protease, lytic enzyme, mutase, mutastein, sorbic acid, alexin, $\beta$-glycyrrhetinic acid, hinokitiol, dihydrocholesterol, epidihydrocholesterol, alkyl glycine, alkyldiaminoethylglycine salt, allantoin, $\epsilon$-aminocaproic acid, tranexamic acid, azulene, other vitamins, water soluble salt of phosphoric acid (mono- or dibasic), quaternary ammonium compound (e.g., cetylpyridinium chloride), sodium chloride, active components (e.g., crude drug extracts), or the like.

The present oral composition can be produced in any form, for example, a dentifrice (e.g., paste dentifrice, powdery dentifrice, wet tooth powder, or liquid tooth powder), an oral detergent (e.g., mouth wash), a topical application, an oral refrigerant, or a collutory (e.g., chewing gum, dental floss, troche).

In the present oral composition, the pH value is not critical, but is preferably 3-10, more preferably 4-9, most preferably 5-7.

EXPERIMENTS

The caries prevention effect of the present oral composition will be illustrated hereinafter.

Experiment 1

Sodium fluoride and the heterocyclic compounds or the fatty acid ester (for comparison) listed in Tables 1 to 3 were added to an distilled water in the amounts shown in Tables 1 to 3, and the pH of the solution was adjusted to 4.5 with dilute hydrochloride or sodium hydroxide to form several preparations. Synthetic hydroxyapatite powder was incubated in each of the preparations at 37° C. for 5 minutes and in a calcifying solution at 37° C. for 60 minutes, and then filtrated and dried. The fluorine concentration in the treated synthetic hydroxyapatite powder was determined by microdiffusion analysis, and the amount of dissolved calcium after incubating the treated powder in an acetate buffer at 37° C. for 60 minutes was measured. The inhibition (%) of decalcification was then calculated by the following equation, to evaluate the acid resistance thereof.

$$\text{Inhibition of decalcification (\%)} = \left(1 - \frac{\text{Amount of dissolved Ca of tested group}}{\text{Amount of dissolved Ca of control group}}\right) \times 100$$

The results are shown in Tables 1 to 3.

TABLE 1

| Sodium fluoride (%) | Pyridoxine hydrochloride (%) | Fluorine concentration (ppm) | Inhibition of decalcification (%) |
| --- | --- | --- | --- |
| 0 (distilled water) | 0 | 34 | — |
| 0.2 | 0 | 4910 | 40.9 |
| 0.2 (molar ratio about 1:0.2) | 0.2 | 14071 | 61.2 |

TABLE 1-continued

| Sodium fluoride (%) | Pyridoxine hydrochloride (%) | Fluorine concentration (ppm) | Inhibition of decalcification (%) |
| --- | --- | --- | --- |
| 0.2 (molar ratio about 1:1) | 1.0 | 20320 | 72.1 |
| 0.2 (molar ratio about 1:2) | 2.0 | 23620 | 73.9 |
| 0.2 (molar ratio about 1:3) | 3.0 | 27120 | 74.4 |

TABLE 2

| | Fluorine concentration (ppm) | Inhibition of decalcification (%) |
| --- | --- | --- |
| Distilled water | 34 | — |
| Sodium fluoride 0.2% | 4910 | 40.9 |
| Sodium fluoride 0.2% + 3-pyridylcarbinol 0.52% (molar ratio about 1:1) | 21187 | 72.1 |
| Sodium fluoride 0.2% + nicotinic acid 0.59% (molar ratio about 1:1) | 18765 | 70.1 |
| Sodium fluoride 0.2% + nicotinic acid amide 0.58% (molar ratio about 1:1) | 9891 | 53.0 |
| Sodium fluoride 0.2% + methyl nicotinate 0.65% (molar ratio about 1:1) | 16255 | 65.0 |

TABLE 3

| | Fluorine concentration (ppm) | Inhibition of decalcification (%) |
| --- | --- | --- |
| Distilled water | 33 | — |
| Sodium fluoride 0.2% | 4796 | 40.9 |
| Sodium fluoride 0.2% + thiamine hydrochloride 1.59% (molar ratio about 1:1) | 22840 | 75.8 |
| Sodium fluoride 0.2% + acrinol 1.70% (molar ratio about 1:1) | 13026 | 68.2 |
| Sodium fluoride 0.2% + histidine hydrochloride 0.96% (molar ratio about 1:1) | 11668 | 62.3 |
| Sodium fluoride 0.2% + sucrose fatty acid ester 3.12% (molar ratio about 1:1) | 6921 | 48.0 |

The above data indicates that the synthetic hydroxyapatite includes more fluorine and has a higher resistance to acid when sodium fluoride is used in combination with the fatty acid ester, in particular the above heterocyclic compounds, in comparison with the use of sodium fluoride alone, and accordingly, the reinforcement of the effect of sodium fluoride by the heterocyclic compounds was confirmed.

Experiment 2

A fluoride compound, and pyridoxine hydrochloride, 3-pyridylcarbinol or thiamine hydrochloride were added to distilled water, in amounts shown in table 4 to produce preparations. A bovine tooth (which had been ground to remove 200 μm of the surface and expose the enamel surface) was incubated in each preparation at 37° C. for 5 minutes and in a calcifying solution at 37° C. for 60 minutes, and then washed with tap water and dried. The fluorine concentration in the enamel of the fluoride-treated bovine tooth was determined by enamel biopsy. The fluoride-treated bovine tooth was dipped in an acidic gelatin gel prepared by the procedure disclosed in Leon M. Silverstone, Caries Research, 1 261–274, 1967, then after 4, 8, and 15 weeks, the amount of decalcification was observed by microradiography, and the acid resistance was evaluated by the following ratings.

ⓞ... Decalcification substantially inhibited.
◦... Decalcification acceptably inhibited.
Δ... Considerable decalcification.
x... No inhibition of decalcification.

The results are shown in Table 4.

TABLE 4

| Preparation | | Distilled water | Sodium fluoride (2%) | Sodium fluoride (2%) + pyridoxine hydrochloride (10%) (molar ratio 1:1) | Sodium fluoride (2%) + 3-pyridylcarbinol (5.2%) (molar ratio 1:1) | Sodium fluoride (2%) + thiamine hydrochloride (15%) (molar ratio 1:1) |
|---|---|---|---|---|---|---|
| F conc. in enamel | 1st Etch | 38 ppm (10.2 μm) | 498 ppm (9.2 μm) | 14988 ppm (1.8 μm) | 15033 ppm (1.7 μm) | 16001 ppm (1.5 μm) |
| | 2nd | 35 ppm (21.5 μm) | 309 ppm (20.0 μm) | 7859 ppm (5.1 μm) | 8001 ppm (4.9 μm) | 7569 ppm (5.1 μm) |
| | 3rd | 34 ppm (33.7 μm) | 222 ppm (32.6 μm) | 4522 ppm (9.3 μm) | 4655 ppm (9.0 μm) | 4431 ppm (9.0 μm) |
| | 4th | 33 ppm (46.3 μm) | 178 ppm (46.5 μm) | 3225 ppm (14.7 μm) | 3211 ppm (14.1 μm) | 2988 ppm (14.1 μm) |
| | 5th | 30 ppm (60.0 μm) | 139.pp. (61.6 μm) | 2985 ppm (22.6 μm) | 3102 ppm (21.5 μm) | 2847 ppm (22.4 μm) |
| Inhibition of decalcification | 4 W | x | ◦ | ⓞ | ⓞ | ⓞ |
| | 8 W | x | Δ | ⓞ | ⓞ | ⓞ |
| | 15 W | x | x | ◦ | ◦ | ◦ |

The above data indicates that the bovine enamel includes more fluorine and has a higher inhibition of decalcification when sodium fluoride is used in combination with the above heterocyclic compounds, in comparison with the use of sodium fluoride alone, and accordingly, the reinforcement of the effect of sodium fluoride by the heterocyclic compounds was confirmed.

It is obvious from Experiments 1 and 2 that the present oral composition is a very useful composition for enhancing a conventional effect of preventing caries with fluoride, by employing the fluoride compound in combination with one or more nitrogen-heterocyclic compounds.

EXAMPLES

The present invention now will be further illustrated by, but is by no means limited to, the following Examples. In the following Examples, the amounts of the ingredients incorporated are percentage by weight.

EXAMPLE 1

Paste dentifrice

In accordance with a conventional procedure, a paste dentifrice was prepared from the following composition:

| | |
|---|---|
| Calcium phosphate (dibasic) dihydrate | 40.0 |
| Glycerol | 10.0 |
| Sorbitol | 10.0 |
| Sodium carboxymethyl cellulose | 1.5 |
| Sodium lauryl sulfate | 1.5 |
| Sodium saccharin | 0.1 |
| Perfume | 1.0 |
| Sodium monofluorophosphate | 0.76 |
| Pyridoxine hydrochloride | 1.0 |
| Purified water | q.s. |

EXAMPLE 2

The procedure of Example 1 was repeated, except that 0.52% by weight of 3-pyridylcarbinol was used instead of 1.0% by weight of pyridoxin hydrochloride.

EXAMPLE 3

The procedure of Example 1 was repeated, except that 1.5% by weight of thiamine hydrochloride was used instead of 1.0% by weight of pyridoxin hydrochloride.

COMPARATIVE EXAMPLE 1

The procedure of Example 1 was repeated, except that pyridoxin hydrochloride was omitted.

COMPARATIVE EXAMPLE 2

The procedure of Example 1 was repeated, except that sodium monofluorophosphate and pyridoxin hydrochloride were omitted.

The paste dentifrices of Examples 1 to 3 and Comparative Examples 1 to 2 were diluted 10 times with distilled water, and a human tooth was incubated in each diluted liquid at 37° C. for 60 minutes, thoroughly washed, and dried. An enamel powder was obtained from the treated human tooth. The fluorine concentration in the enamel powder was determined by a microdiffusion analysis, and the amount of dissolved calcium after incubating the treated human tooth in an acetate buffer at 37° C. for 60 minutes was measured. The inhibition (%) of decalcification was calculated by the following equation, to evaluate the acid resistance thereof.

$$\text{Inhibition of decalcification (\%)} = \left(1 - \frac{\text{Amount of dissolved Ca of tested group}}{\text{Amount of dissolved Ca of control group}}\right) \times 100$$

The results are shown in Table 5.

TABLE 5

| Paste dentifrice | Fluorine concentration (ppm) | Inhibition of decalcification (%) |
|---|---|---|
| Example 1 | 1428 | 45.8 |
| Example 2 | 1563 | 47.5 |
| Example 3 | 1623 | 50.5 |
| Comparative Example 1 | 620 | 29.1 |
| Comparative Example 2 | 42 | 0.1 |

It is apparent from Table 5 that the paste dentifrices according to the present invention exhibit a very high fluorine trapping effect and inhibition of decalcification, in comparison with the comparative paste dentifrices.

EXAMPLE 4

Paste dentirice

In accordance with the conventional procedure, a paste dentifrice was prepared from the following composition:

| Silicic acid anhydride | 20.0 |
|---|---|
| Sorbitol | 50.0 |
| Carrageenan | 0.5 |
| Sodium carboxymethyl cellulose | 1.0 |
| Sodium lauryl sulfate | 1.8 |
| Sodium saccharin | 0.08 |
| Methyl paraoxybenzoate | 0.2 |
| Perfume | 0.9 |
| Sodium fluoride | 0.2 |
| Pyridoxine hydrochloride | 0.2 |
| Purified water | q.s. |

The above procedure was repeated, except that 0.2% by weight of pyridoxine hydrochloride was replaced by 0.5% by weight of nicotinic acid or 1.6% by weight of acrinol.

EXAMPLE 5

Paste dentifrice

In accordance with a conventional procedure, a paste dentifrice was prepared from the following composition:

| Sorbitol | 20.0 |
|---|---|
| Silicic acid anhydride | 50.0 |
| Sodium polyacrylate | 0.7 |
| Sodium lauryl sulfate | 1.8 |
| Triethanolamine | 0.5 |
| Sodium saccharin | 0.1 |
| Sodium paraoxybenzoate | 0.2 |
| Perfume | 0.9 |
| Sodium monofluorophosphate | 0.76 |
| Pyridoxine hydrochloride | 0.2 |
| Allantoin | 1.0 |
| Purified water | q.s. |

The above procedure was repeated, except that 0.2% by weight of pyridoxine hydrochloride was replaced by 0.3% by weight of nicotinic acid amide, or 1.0% by weight of histidine hydrochloride and 0.2% by weight of pyridoxine hydrochloride.

EXAMPLE 6

Mouth wash

In accordance with a conventional procedure, a mouth wash was prepared from the following composition:

| Ethylalcohol | 10.0 |
|---|---|
| Sodium saccharin | 0.05 |
| Perfume | 0.8 |
| Polyoxyethylene (20 mole) sorbitan lauric acid ester | 1.0 |
| Sodium fluoride | 0.02 |
| Pyridoxine hydrochloride | 0.02 |
| Purified water | q.s. |

The above procedure was repeated, except that 0.02% by weight of pyridoxine hydrochloride was replaced by 1.0% by weight of nicotinic acid amide, or 0.5% by weight of thiamine hydrochloride.

EXAMPLE 7

Mouth detergent

In accordance with a conventional procedure, a mouth detergent was prepared from the following composition:

| Sodium fluoride | 0.05 |
|---|---|
| Pyridoxine hydrochloride | 0.02 |
| Sodium phosphate (dibasic) | 0.3 |
| Sodium phosphate (monobasic) | 0.7 |
| Perfume | 0.5 |
| Sodium saccharin | 0.02 |
| Purified water | q.s. |

The above procedure was repeated, except that 0.02% by weight of pyridoxine hydrochloride was replaced by 0.5% by weight of 3-pyridylcarbinol, or 0.2% by weight of thiamine hydrochloride.

EXAMPLE 8

Topical application

In accordance with a conventional procedure, a topical application was prepared from the following composition:

| Sodium fluoride | 2.0 |
|---|---|
| Pyridoxine hydrochloride | 1.0 |
| Perfume | 0.5 |
| Sodium saccharin | 0.02 |
| Purified water | q.s. |

The above procedure was repeated, except that 1.0% by weight of pyridoxine hydrochloride was replaced by 1.0% by weight of 3-pyridylcarbinol, or 5.0% by weight of thiamine hydrochloride.

EXAMPLE 9

Oral refrigerant (spray type)

In accordance with a conventional procedure, an oral refrigerant was prepared from the following composition:

| Ethylalcohol | 40.0 |
|---|---|
| Sodium saccharin | 0.1 |
| Sorbitol | 10.0 |
| Perfume | 1.0 |
| Polyoxyethylene (60 mole) hardened castor oil | 0.7 |
| Chlorohexdine hydrochloride | 0.05 |
| Sodium fluoride | 0.05 |
| Pyridoxine hydrochloride | 0.5 |
| Purified water | q.s. |

The above procedure was repeated, except that 0.5% by weight of pyridoxine hydrochloride was replaced by 0.5% by eight of methyl nicotinate, or 0.2% by weight of thiamine hydrochloride.

EXAMPLE 10

Chewing gum

In accordance with a conventional procedure, a chewing gum was prepared form the following composition:

| Gum base | 25.0 |
|---|---|

-continued

| | |
|---|---|
| Calcium carbonate | 2.0 |
| Perfume | 1.0 |
| Copper chlorophyll | 0.05 |
| Sodium fluoride | 0.2 |
| Pyridoxine hydrochloride | 1.0 |
| Sorbitol | q.s. |

The above procedure was repeated, except that 1.0% by weight of pyridoxine hydrochloride was replaced by 0.1% by weight of ethyl nicotinate, or 1.0% by weight of thiamine hydrochloride.

Although the present invention has been described with reference to specific embodiments, various changes and modifications obvious to those skilled in the art are deemed to be within the spirit, scope and conceit of the invention.

We claim:

1. A method of enhancing a prevention of caries of the teeth, comprising applying to the teeth a composition comparison (i) at least one inorganic fluoride compound nd (ii) at lest one nitrogen-heterocyclic compound selected from the group consisting of pyridoxine, pyridoxal, pyridoxamine, and salts thereof; pyridyl carbinol; thiamine and salts thereof; histidine and salts thereof; and nicotinic acid and nicotinic acid amide.

2. A mdethode as claimed in claim 1, wherein the nitroge-heterocyclic compound is at least one compound selected form the group consisting of pyridoxine, pyridoxal, pyridoxamine and salts thereof.

3. A method as claimed in claim 1, wherein the nitrogen-heterocyclic compound is pyridyl carbinol, 4. A method as claimed in claim 1, wherein the nitrogen-heterocyclic compound is at least one compound selected from the group consisting of thiamine and salts thereof.

5. A method as claimed in claim 1, wherein the nitrogen-heterocyclic compound is at least one compound selected form the group consisting of histidine and salts thereof.

6. A method as claimed in claim 1, wherein the nitrogen-gheterocyclic compound is at least one compound selected from the group consisting of nicotinic acid and nicotinic acid amide.

7. A method as in claim 1, wherein the amount of fluoride compound incorporated is from about 50 to about 10,000 µg per gram of the composition as a total fluorine concentration, and the molar ratio of the nitrogen-heterocyclic compound to the fluoride compound is from about 1/50 to about 10/1.

8. A method as claimed n claim 1, said composition further comprising at least one additive selected from the group consisting of a polishing agent, wetting agent, thickening agent, surface active agent, oil, edulcorant, essential oil, perfume colorant, preservative, antimold agent, antioxidant, and water.

9. A method as claimed in claim 7, wherein the nitrogen-heterocyclic compound is pyridoxine hydrochloride.

10. A method as claimed in claim 25, wherein the nitrogen-heterocyclic compound is at least one compound selected from the group consisting of pyridoxine and salts thereof.

* * * * *

UNITED STATES PATENT AND TRADEMARK OFFICE
CERTIFICATE OF CORRECTION

PATENT NO. : 5,174,989
DATED : December 29, 1992
INVENTOR(S) : Tanaka et al.

It is certified that error appears in the above-identified patent and that said Letters Patent is hereby corrected as shown below:

Col. 11, line 21    Delete " comparison " and substitute -- comprising --

Col. 11, line 22    Delete " nd " and substitute -- and --; delete " lest " and substitute -- least --

Col. 11, line 27    Delete " mdethode " and substitute method --

Col. 11, line 28    Delete " nitroge " and substitute -- nitrogen --

Col. 12, line 10    Delete " gheterocyclic " and substitute -- heterocyclic --

Col. 12, line 14    Before " fluoride " insert -- the --

Col. 12, line 19    Delete " n " and substitute -- in --

Col. 12, line 28    Delete " claim 25 " and substitute -- claim 1 --

Signed and Sealed this

Thirty-first Day of May, 1994

Attest:

BRUCE LEHMAN

*Attesting Officer*    *Commissioner of Patents and Trademarks*